(12) United States Patent
Casutt

(10) Patent No.: US 6,659,997 B1
(45) Date of Patent: Dec. 9, 2003

(54) OPERATING TOOL

(75) Inventor: Simon Casutt, Gossau (CH)

(73) Assignee: Sulzer Orthopedics Ltd., Baar (CH)

( * ) Notice: Subject to any disclaimer, the term of this patent is extended or adjusted under 35 U.S.C. 154(b) by 285 days.

(21) Appl. No.: 09/699,010

(22) Filed: Oct. 27, 2000

(30) Foreign Application Priority Data

Nov. 26, 1999 (EP) .............................................. 99811092

(51) Int. Cl.[7] .............................................. A61B 17/00
(52) U.S. Cl. ........................... 606/1; 16/422; 81/177.85
(58) Field of Search ..................... 606/1; 81/52, 177.1, 81/177.85; 16/110.1, 421, 422; 403/321, 325, 326, 332, DIG. 4

(56) References Cited

U.S. PATENT DOCUMENTS

| 1,052,077 | A | * | 2/1913 | McMillan ................. 16/422 X |
| 1,630,239 | A | | 5/1927 | Binkely |
| 2,288,584 | A | | 6/1942 | Longfellow |
| 2,574,330 | A | * | 11/1951 | Judd ......................... 16/422 X |
| 3,461,874 | A | * | 8/1969 | Martinez ....................... 606/1 |
| 3,803,667 | A | * | 4/1974 | Rose ............................... 606/1 |
| 5,507,738 | A | * | 4/1996 | Ciervo ........................... 606/1 |
| 5,638,577 | A | * | 6/1997 | Gooding et al. .............. 16/422 |
| 5,993,470 | A | * | 11/1999 | Yoon ......................... 606/1 X |
| 6,273,882 | B1 | * | 8/2001 | Whittier et al. ................ 606/1 |

FOREIGN PATENT DOCUMENTS

| FR | 2702172 | | 9/1994 |
| GB | 943610 | | 12/1963 |
| WO | 98/17922 | * | 4/1998 |

* cited by examiner

Primary Examiner—John Rivell
(74) Attorney, Agent, or Firm—Townsend and Townsend and Crew, LLP

(57) ABSTRACT

An operating tool (1, 1a) for use in the operating room comprises a grip part (2, 2a) and a tool part (3, 3a) which is firmly connected to this grip part (2, 2a), with the connection of the grip part (2, 2a) and the tool part (3, 3a) being formed as a releasable connection.

10 Claims, 4 Drawing Sheets

Fig.6
Fig.7
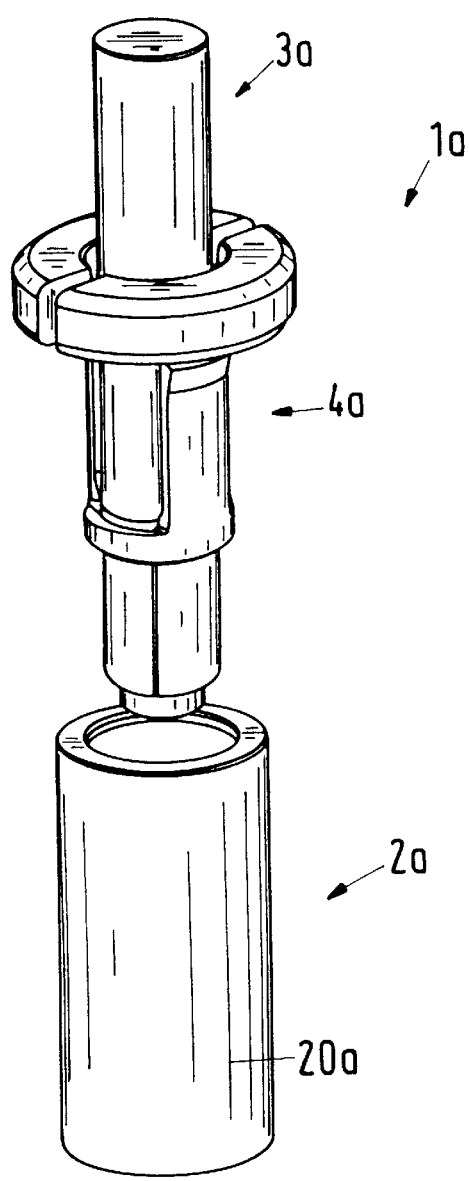
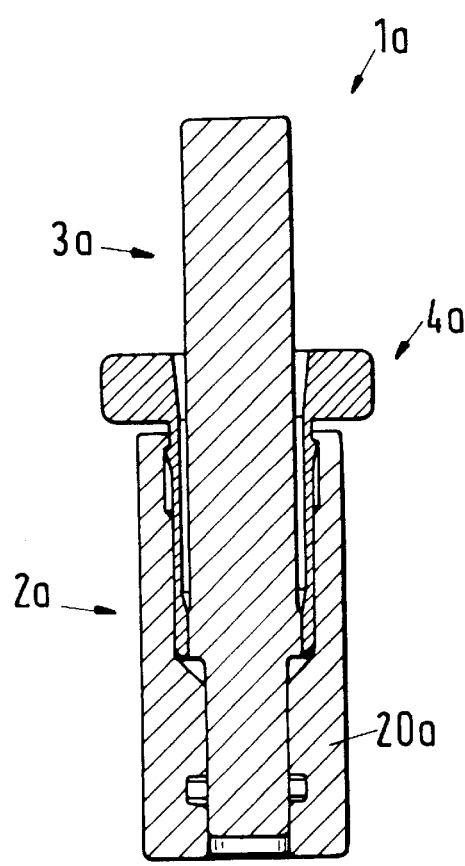

OPERATING TOOL

BACKGROUND OF THE INVENTION

The invention relates to an operating tool for use in the operating room. Operating tools of this kind basically have a grip part which the operating surgeon grips and by means of which he can use the tool, as well as a tool part by means of which the treatment takes place. The grip part and the tool part are firmly connected to one another.

Operating tools for use in the operating room are available in innumerable embodiments. The tools, which differ greatly depending on their field of use, must be simple and easy to clean and sterilize after an operation insofar as they are reusable tools.

Already existing operating tools have grip parts of a hard plastic which are formed very differently depending on their field of use. Existing grip parts can be subdivided into different types, of which several will be named in an exemplary manner in the following. An example of such a type of grip part is a screwdriver grip, that is, an elongate, profiled grip part by means of which in particular pressing forces and torques can be exerted. A further example of such a grip part is the so-called T-grip, by means of which in particular draw forces and torques can be exerted. Another example of such a grip part is the bulb grip, by means of which in particular pressing forces and laterally directed leverages can be exerted. Another different example of such a grip part is the probe grip, a substantially non-profiled elongate grip which is suitable in particular for uses in which certain conditions are probed. Moreover, there are a number of still different types of grips, which cannot all be listed here individually.

In already existing operating tools it is the case that the tool parts and the grip parts are connected to one another not only firmly but moreover also unreleasably. Frequently the tool parts, which typically consist of stainless steel or another non-rusting material, have been cast into the grip part, which typically consists of plastic, or have been injection molded in the plastic of the grip part. Operating tools of this kind can be cleaned (e.g. by means of ultrasonic baths) and also sterilized (e.g. through vapor sterilization) in a simple and reliable way.

The innumerable designs of the different kinds of operating tools, which must then be present regularly in several different sizes, require a high stocking expenditure because each tool part must be stocked with its associated grip part in the different sizes. It is frequently even the case that one tool part must be present with different types of grip parts since the operating surgeon admittedly requires the same tool part depending on the field of use, but with a different grip part.

Previously a separate operating tool had to be present in each case for each desired combination of grip part and tool part and for every desired size. This increases the storage expenditure yet further, especially when it is taken into account that for each combination of grip part and tool part usually several items must be in stock, not to mention the high acquisition costs which are naturally associated with a correspondingly large number of operating tools.

SUMMARY OF THE INVENTION

It is an object of the invention to propose an operating tool by means of which it is possible to reduce the stocking expenditure for the operating tools considerably, without it being necessary to reduce the variety and availability of the different operating tools. Moreover, the operating tool must be capable of simple and reliable cleaning and sterilization.

The operating tool in accordance with the invention for use in the operating room comprises a grip part and a tool part which is firmly connected to this grip part, with the connection of the grip part and the tool part being formed as a releasable connection.

It is thereby possible to connect a large number of different tool parts with one and the same grip part, through which the stocking is substantially reduced, as only a substantially smaller number of grip parts need be stocked, since quite a number of individual tool parts can be connected to one and the same grip part.

In particular it is also possible to combine a specific tool part with a specific type of grip part depending on the field of use, through which the variety of the operating tools is maintained or is even increased. After use the firm connection of the grip part and the tool part is to be released again and the individual parts are to be cleaned and sterilized. Then the grip part and the tool part are again available for use, with it then being possible to connect a completely different tool part for a completely different field of use to the very same grip part.

A further advantage is that with a sterile storage of the grip parts and the tool parts the operating surgeon can first select a number of tool parts and a number of grip parts prior to the operation which he will possibly require during the operation and then finally assemble the required operating tools only in the operation room, or have them assembled there by assisting personnel.

An advantageous exemplary embodiment of the operating tool in accordance with the invention is equipped with a reception at the distal end of the grip part into which the tool part is introduced, with means being provided at the tool part and at the reception which effect the firm connection of the grip part and the tool part.

This reception for the tool part preferably comprises a sleeve which is manufactured of a hard, low-wear material and which is unreleasably connected to the grip part. The sleeve can e.g. be manufactured of ceramics or of a hard, low-wear plastic. Preferably, it is however manufactured of a hard, low-wear non-rusting metal such as e.g. of a stainless steel and can be cast or injection molded into a plastic which forms the hand grip so that the entire grip part can be reliably cleaned and sterilized. The separate manufacturability of the sleeve and the casting or injection molding into a plastic, which only takes place after this manufacture, also means a simplification from the manufacturing side.

The connection of the grip part and the tool part can in principle be formed in the most diverse manners. In an advantageous embodiment however the connection of the grip part and the tool part is formed as a screw connection. This is on the one hand a reliable connection, and on the other hand a simply releasable and also reliably producible connection.

In a further development of this exemplary embodiment the grip part or the sleeve respectively has an abutment for the proximal end of the tool part. The screw connection comprises a clasping collar with an outer thread and an inner thread in the grip part or in the sleeve respectively which cooperates with this outer thread of the clasping collar. The clasping collar surrounds the tool part and can be moved along the tool part in the direction of the longitudinal axis of the tool part until abutment means which are provided at the tool part and at the clasping collar abut against one another.

In this further development the tool part can first be introduced into the grip part or into the sleeve respectively until the proximal end of the tool part strikes against the abutment which is provided in the grip part or in the sleeve respectively. Then the outer thread of the clasping collar can be screwed into the inner thread in the grip part or in the sleeve respectively until the abutment means of the clasping collar strike against the abutment means at the tool part so that the tool part is then secured against axial displaceability.

In an advantageous further development of this exemplary embodiment both the abutment in the grip part or in the sleeve respectively and the proximal end of the tool part are designed circularly conically. Furthermore, the clasping collar is provided at its proximal end with the outer thread and has at its distal end an inwardly directed projection. This projection protrudes into a cut-out on the outside of the tool part so that it limits the movement of the clasping collar in the direction of the longitudinal axis of the tool part.

The circularly conical construction of the proximal end of the tool part and of the abutment in the grip part or in the sleeve respectively effect a centering of the tool part in the introduction of the tool part into the grip part. After the introduction of the tool part the outer thread of the clasping collar is screwed into the inner thread of the grip part or of the sleeve respectively. Through this the projection which projects inwardly from the clasping collar is moved together with the clasping collar along the tool part in the direction of the longitudinal axis of the tool part, and indeed in the proximal direction. The screwing in of the clasping collar continues until the projection which projects inwardly from the clasping collar prevents a further screwing in of the clasping collar because it e.g. abuts against an end surface of the cut-out. The tool part is then secured against axial displaceability and is centered at the same time.

As already mentioned, the connection of the grip part and the tool part can be formed in the most diverse of manners. In a further exemplary embodiment the connection of the grip part and the tool part is accordingly formed as a snap connection. This kind of connection is likewise a reliable connection which can be simply released and reliably produced.

In a further development of this exemplary embodiment the snap connection has a clasping collar which is firmly connected to the tool part and which is provided with resilient lamella. These resilient lamella have in each case a projection which is in engagement with a corresponding projection at the distal end of the grip part or of the sleeve respectively. In the further course the lamella project in the distal direction out of the grip part and are provided outside the grip part with a member for pressing together the lamella in order to be able to effect a releasing of the projections which are in engagement with one another. This exemplary embodiment is distinguished in that both the introduction of the tool part into the grip part and the production of a firm connection of the grip part and the tool part is possible in a simple and reliable manner. Likewise the releasing of the snap connection and the removal of the tool part from the grip part is very simply possible. Finally, the clasping collar can be manufactured as a separate part and be connected to the tool part only later, for example through welding, which simplifies the manufacture of the individual parts.

In all previously named exemplary embodiments both the grip part or the sleeve respectively and the tool part have in each case a region which is constructed to be non-rotationally symmetric. These regions are designed to fit together with one another in regard to their shape and to their dimensions, and the non-rotationally symmetrical region of the grip part or of the sleeve respectively surrounds the corresponding non-rotationally symmetrical region of the tool part in order to be able to transmit a torque. Thus the axial securing of the tool part in the grip part against a sliding out and the transmission of torques are functionally separate from one another.

In a further development the non-rotationally symmetrical region has a rectangular, preferably square, cross-section. A cross-section of this kind is simple to manufacture and is well suited for the transmission of torques.

The operating tool set in accordance with the invention comprises at least one grip part and a plurality of tool parts, with the tool parts being designed in their proximal region in such a manner that different tool parts can be received by one and the same grip part and firmly connected to the latter. Through this the tool variety is maintained or even increased and at the same time the stocking expenditure is reduced. As already explained above, the surgeon can even select prior to the operation a number of grip parts and a number of tool parts which he will possibly require in the operation and then finally assemble the desired combination of grip part and tool part only in the operation room, or have them assembled there by assisting personnel.

The invention will be explained in the following in more detail with reference to the drawings.

BRIEF DESCRIPTION OF THE DRAWINGS

FIG. 6 shows a second exemplary embodiment of an operating tool in accordance with the invention, with the grip part and the tool part not yet being connected to one another, FIG. 7 shows the exemplary embodiment of the operating tool of FIG. 6, with the grip part and the tool part being firmly, but releasably, connected to one another with the help of a snap collar.

DESCRIPTION OF THE PREFERRED EMBODIMENT

Figure 1:
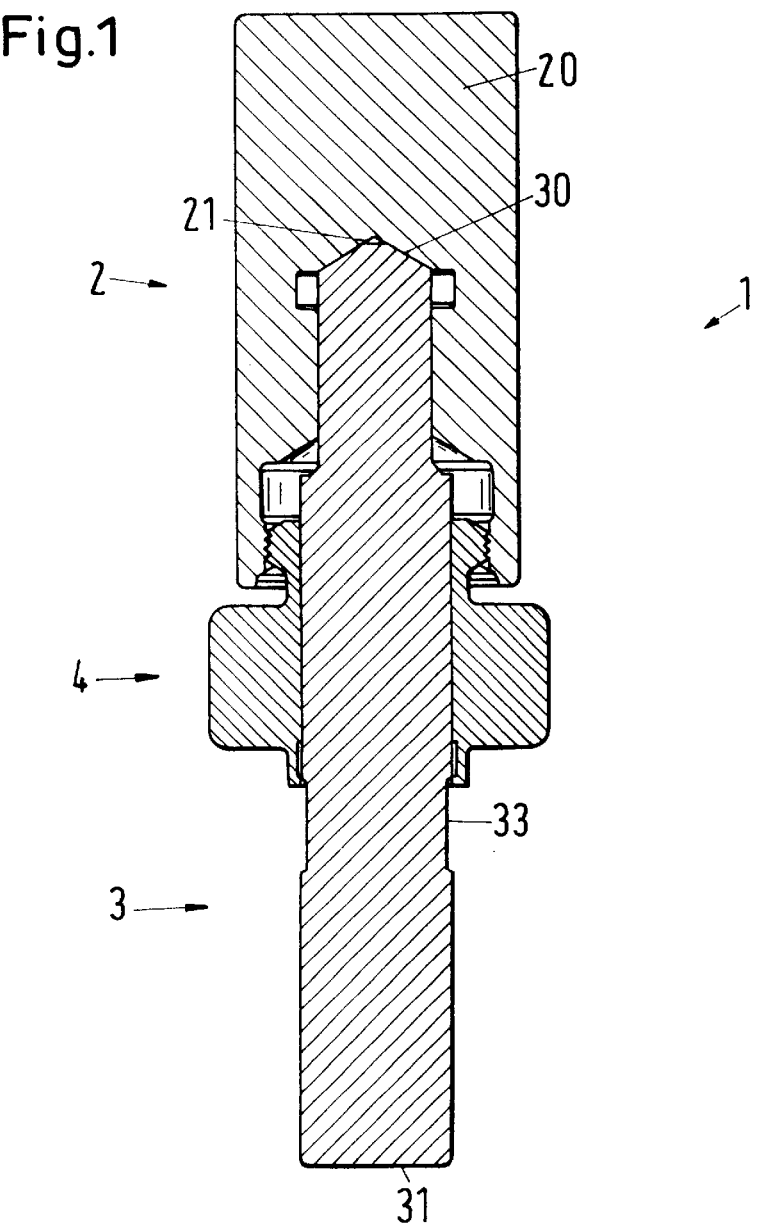
FIG. 1 shows a, first exemplary embodiment of an operating tool in accordance with the invention in which the grip part and the tool part are firmly, but releasably, connected to one another with the help of a clasping collar.
Figure 2:
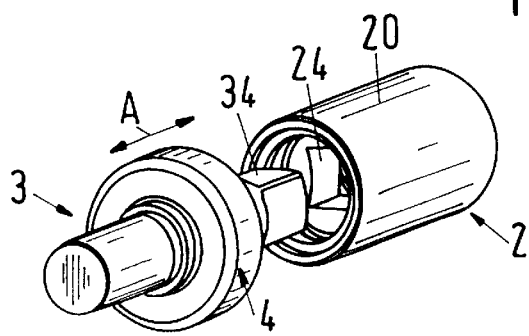
FIG. 2 shows the exemplary embodiment of the operating tool of FIG. 1, with however the grip part and the tool part not yet being connected to one another.

In FIG. 1 and FIG. 2 a first exemplary embodiment of an operating tool 1 according to the present invention is illustrated, with FIG. 1 showing an illustration of the assembled operating tool in an illustration in longitudinal section, and FIG. 2 showing a perspective illustration of the operating tool 1 in which the grip part 2 and the tool part 3 are not connected to one another. The operating tool 1 comprises the already mentioned grip part 2 and the tool part 3 as well as a clasping collar 4. The individual parts will be described more precisely with reference to FIG. 3, FIG. 4 and FIG. 5.

From FIG. 1 one recognizes that the firm but releasable connection of the grip part 2 and the tool part 3 is formed as a screw connection. In FIG. 1 only a sleeve 20 of the grip part 2, which is manufactured of a hard, low-wear material, e.g. stainless steel, and which represents a reception for the proximal end 30 of the tool part 3 (see also FIG. 4) can be recognized (see also FIG. 6). This sleeve 20 is non-releasably connected to the grip part 2 in that it for example can be injection molded or cast in a plastic (not illustrated). For graphic reasons however only the sleeve 20 is illustrated, since the plastic which surrounds the sleeve is irrelevant for the connection between the tool part 3 and the grip part 2.

In principle the sleeve 20 of the grip part 2, the tool part 3 and the clasping collar 4 are separately manufacturable parts, which will be described with reference to FIG. 3, FIG. 4 and FIG. 5. After the manufacture however the clasping collar 4 is connected to the tool part in a manner which remains to be described, so that the combination of the tool part 3 and the clasping collar 4 can then be inserted together into the sleeve 20 of the grip part 2 or, respectively, after a completed use of the operating tool can also be released again together from the sleeve 20 of the grip part 3. This is also symbolically indicated by the arrows A in FIG. 2.

Figure 3:
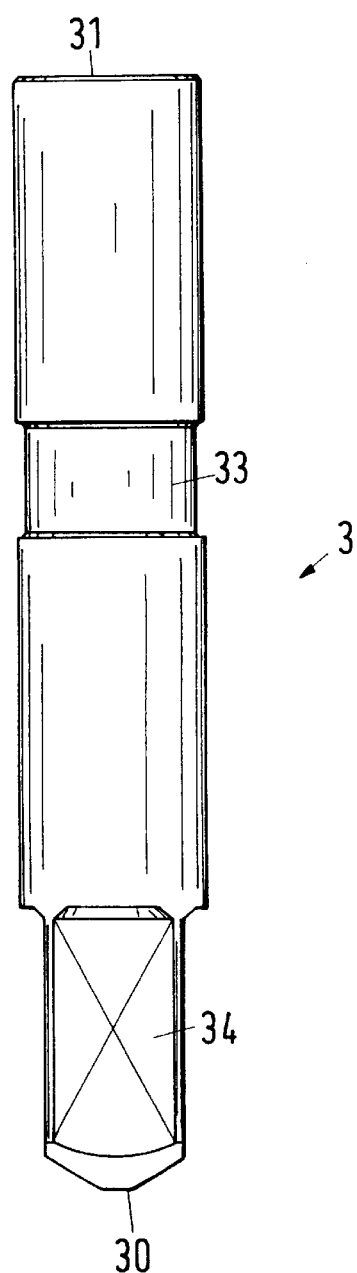
FIG. 3 shows the tool part of the operating tool of FIG. 1 without the clasping collar.

In FIG. 3 the tool part 3 can be recognized, with the distal end 31 of the tool part being symbolically illustrated here only as the stud of a shaft. At this distal end 31 of the tool part e.g. the blade of a screwdriver or a probe tip or a hook or many other things can be formed on. The proximal end 30 of the tool part 3 is designed to be circularly conical and cooperates with a correspondingly circular conically formed abutment 21 in the sleeve 20. Through this the tool part 3 is centered during the introduction into the sleeve 20 and thus into the grip part 2. As has already been mentioned, however, the clasping collar 4, which is of course a part which can be manufactured separately, is connected to the tool part prior to the introduction of the tool part 3 into the grip part 2 or into the sleeve 20 respectively.

Figure 4:
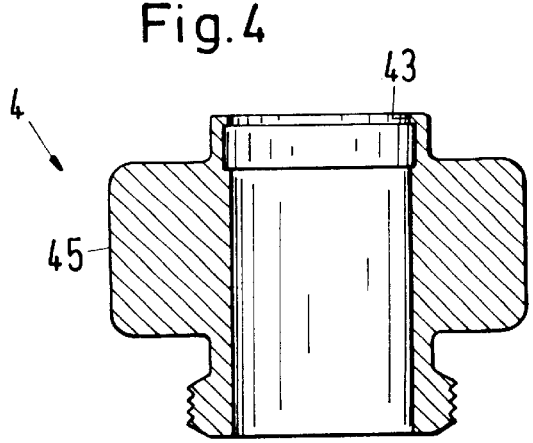
FIG. 4 shows the clasping collar of the operating tool of FIG. 1.

If FIG. 4, in which the clasping collar is illustrated, is considered for this then one recognizes that the clasping collar 4 has an outer thread 42 at its proximal end which can be screwed into a corresponding inner thread 22 in the sleeve 20. For "securing" the clasping collar 4 to the tool part 3 the clasping collar 4 has at its distal end a circumferential projection 43. Accordingly, a cut-out 33 is provided at the tool part. For "securing" the clasping collar 4 at the tool part 3 the clasping collar 4 is pushed over the tool part 3 and the circumferential projection 43 of the clasping collar 4 is bent in, e.g. flanged in, into the cut-out 33 of the tool part 3. Then the clasping collar 4 is movable in the scope of the limitation which is represented by the cut-out 33 since the projection 43 abuts after the flanging in at the end of the cut-out 33 of the tool part 3 when it is moved along the outside of the tool part in the direction of the longitudinal axis of the tool part 3. The tool part 3 with the clasping collar 4 which is applied to the tool part 3 can be easily recognized in FIG. 2.

Figure 5:
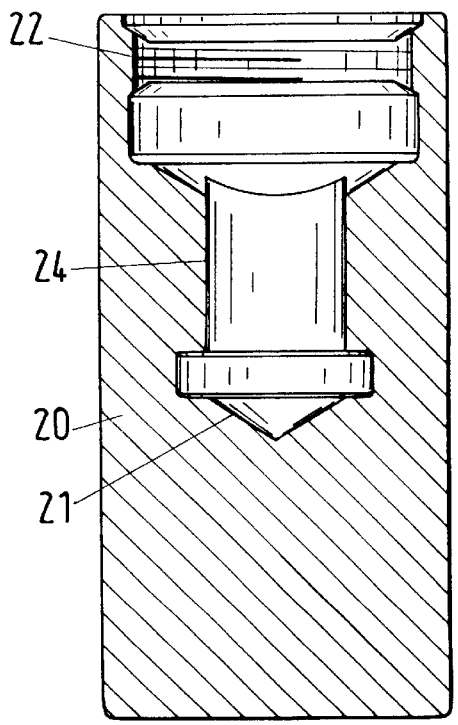
FIG. 5 shows the sleeve of the grip part of the operating tool of FIG. 1.

The sleeve 20 which represents the reception for the tool part 3 can be recognized in FIG. 5. One recognizes the circular cylindrical abutment 21 against which the circular cylindrically formed proximal end of the tool part 3 abuts during the insertion of the tool part 3 into the sleeve 20. In addition one recognizes the inner thread 22 into which the outer thread 42 of the clasping collar 4 engages during the screwing in of the clasping collar 4 into the sleeve 20. Finally, the sleeve 20 has another region 24 which is designed as a square and which during the introduction of the tool part 3 into the sleeve 20 cooperates with a region 34 of the tool part which is likewise designed as a square and is designed to fit together with the region 24 of the sleeve 20 with respect to its shape and dimensions in order to be able to transmit a torque after the introduction of the tool part 3 into the sleeve 20 (and thus into the grip part). In principle a different mutually fitting, non-rotationally symmetrical design of the region 24 of the sleeve 20 and of the region 34 of the tool part 3 is also possible in order to be able to transmit a torque. The square described here can however be manufactured in a simple and reliable way.

The individual parts, which can all be manufactured separately, are—as has partly already been explained—connected in the following way to form an operating tool. First the clasping collar 4 is pushed over the tool part 3 until the inwardly directed projection 43 at the distal end comes to lie over the cut-out 33. Then the projection 43 is bent in, e.g. flanged in, into the cut-out 33 so that the clasping collar 4 can be moved along the outside of the tool part in the direction of the longitudinal axis of the tool part 3 within the scope of the axial extent of the cut-out 33. The tool part 3, which is provided with the clasping collar 4, is then introduced into the sleeve 20 with its proximal end in front, and indeed in such a manner that the region 34 (square) of the tool part 3 fits into the region 24 of the sleeve 20. During the introduction of the tool part 3 a centering first takes place at the proximal end of the tool part 3 since the circular cylindrically formed proximal end 30 of the tool part 3 comes to lie against the circular cylindrically formed abutment 21 of the sleeve 20.

Then the outer thread 42 of the clasping collar 4 is screwed into the inner thread 22 of the sleeve, through which, on the one hand, a centering of the tool part at the distal end of the sleeve 20 also takes place, and in addition the clasping collar 4 is moved in the proximal direction along the longitudinal axis of the tool part 3 as a result of the pitch of the thread. The region 45 of the clasping collar 4 can e.g. be provided with a knurling in order to facilitate the screwing in of the clasping collar 4 into the sleeve 20. The clasping collar 4 is screwed further into the sleeve 20 until the inwardly directed projection 43 abuts against the proximal limit of the cut-out 33 of the tool part 3. The tool part 3 is thus secured (braced) against an axial sliding out and furthermore—as already explained—is also centered. Torques can be transmitted via the square.

A further exemplary embodiment of an operating tool 1a in accordance with the present invention can be recognized in FIG. 6 and FIG. 7, with the individual parts not yet being connected to one another in FIG. 6, whereas in FIG. 7 the individual parts are illustrated to be already connected to one another. In this exemplary embodiment the connection of the tool part 3a and the grip part 2a takes place by means of a snap connection. Here as well the individual parts can in principle be manufactured separately from one another. They will be individually described in the following, and in addition the manner will be described in which the individual parts are connected to one another.

Only the sleeve 20a of the grip part 2a is illustrated in FIG. 6 and FIG. 7 for reasons of draftsmanship, similarly as in the first exemplary embodiment. Again, this sleeve 20a can be cast or injection molded respectively in a plastic and thus form the grip part 2a.

Figure 9:
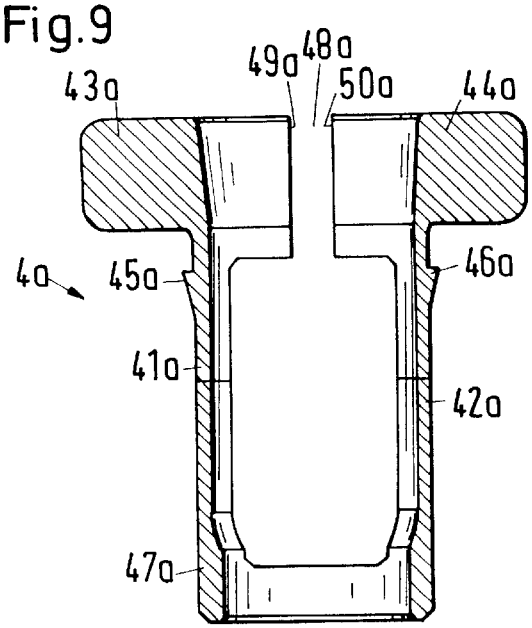
FIG. 9 shows the snap collar of the operating tool of FIG. 6.

The connection of the tool part 3a to the sleeve 20a takes place in this exemplary embodiment with the help of a snap collar 4a. This snap collar 4a is illustrated in FIG. 9 as an individual part. One recognizes that the snap collar 4a is provided with resilient lamella, in this case two lamella 41a and 42a which are connected at their distal end to a member 43a and 44a respectively for pressing together the lamella.

Furthermore, one recognizes two projections 45a and 46a which cooperate with corresponding projections 25a and 26a in the sleeve 20a and form the snap connection. At the proximal end the snap collar 4a has a connection region 47a which is provided for being firmly connected to the tool part 3a, for example through laser welding.

Figure 8:
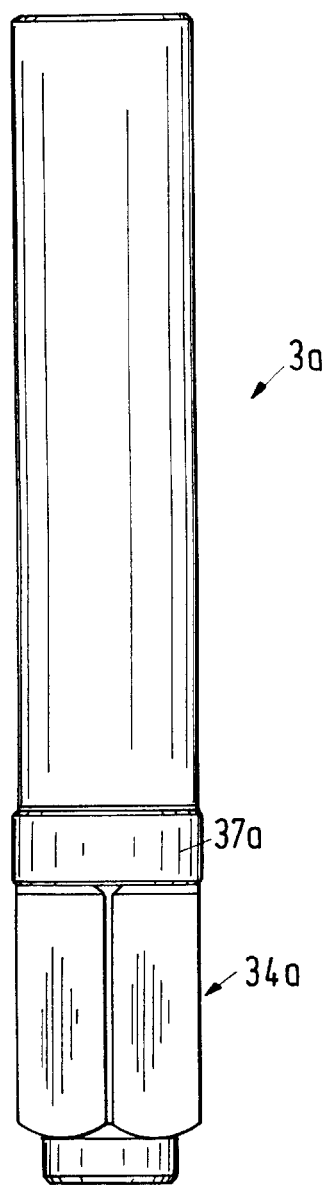
FIG. 8 shows the tool part of the operating tool of FIG. 6 without the snap collar.

The tool part 3a itself can be recognized in FIG. 8 and likewise has a non-rotationally symmetrical region 34a which is formed as a square as in the above-explained exemplary embodiment. Furthermore, the tool part 3a also has a bulge-like connection region 37a which can be firmly connected to the connection region 47a of the snap collar 4a in that for example the connection region 47a is firmly connected to the bulge-like connection region 37a by laser welding.

Figure 10:
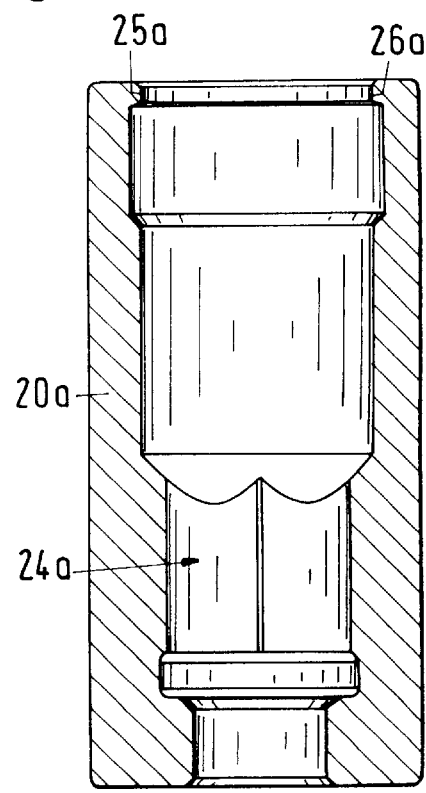
FIG. 10 shows the sleeve of the grip part of the operating tool of FIG. 6.

Finally, one recognizes in FIG. 10 the sleeve 20a, which has a region 24a which is likewise non-rotationally symmetrically designed, here as a square which is designed to fit together with the non-rotationally symmetrical square 34a of the tool part 3a with respect to its shape and dimensions in order to receive the latter in a rotationally fixed manner. Furthermore, the sleeve 20a has two projections 25a and 26a at the distal end which cooperate with the projections 45a and 46a of the lamella 41a and 42a respectively of the snap collar 4a and form the snap connection.

The operating tool is assembled from the separately manufacturable individual parts as follows: First the snap collar 4a is pushed over the tool part 3a until the connection region 47a of the snap collar 4a comes to lie over the bulge-like connection region 37a of the tool part 3a. Then these two parts are firmly connected to one another e.g. through laser welding. Then the tool part 3a is introduced into the sleeve 20a until the two projections 45a and 46a of the lamella 41a and 42a slide over the projections 25a and 26a at the distal end of the sleeve 20a and snap in. Then the tool part 3a is secured against sliding out axially.

For releasing the tool part 3a the two members 43a and 44a are pressed in the direction towards one another, so that the projections 45a and 46a of the snap collar 4a are released from the projections 25a and 26a of the sleeve 20a and at the same time the tool part 3a is drawn out from the sleeve 20a. The slit 48a between the two members 43a and 44a, which are designed as bending springs, is designed in such a manner that an over-stressing of the members 43a and 44a is not possible, since the edges 49a and 50a lie in contact at pressing forces which are too great and thus take up an over-stressing. The tool part 3a with the clasping collar which is secured to it and the grip part 2a with the sleeve 20a can then be cleaned and sterilized. Then for example the same grip part can be combined with a completely different type of tool part or the same tool part can be combined with a completely different type of grip part.

What is claimed is:

1. Operating tool for use in an operating room, comprising a grip part and a tool part which is firmly connected to the grip part, a reception at the distal end of the grip part into which the tool part is introduced, the reception comprising a sleeve which is manufactured of a hard, low-wear material, a connection of the grip part and the tool part being formed as a releasable snap connection, the snap connection having a snap collar which is firmly connected to the tool part and which is provided with resilient lamella which in each case have a projection in engagement with a corresponding projection at a distal end of the grip part, the lamella projecting out of the grip part in a distal direction and being provided outside the grip part with a member for pressing together the lamella to effect a releasing of the projections which are in engagement with one another.

2. Operating tool in accordance with claim 1 wherein the sleeve is non-releasably connected to the grip part.

3. Operating tool in accordance with claim 1, in which both the grip part and the tool part in each case have a region which is formed rotationally non-symmetrical, the regions which are rotationally non-symmetrical fitting together with one another in regard to their shapes and their dimensions and with the rotationally non-symmetrical region of the grip part surrounding a corresponding rotationally non-symmetrical region of the tool part in order to be able to transmit a torque.

4. Operating tool in accordance with claim 3, in which the rotationally non-symmetrical region has one of a rectangular and a square cross-section.

5. An operating tool for use in an operating room, comprising a generally tubular grip part, a tool part including a sleeve made of a hard, low-wear material, and a releasable snap connection which firmly connects the grip part and the tool part, the snap connection including a snap collar firmly secured to the tool part and provided with a resilient lamella extending into the tubular grip part and having a first projection, the grip part having a second projection, the first and second projections snapping into engagement when the lamella extends into the grip part, a portion of the lamella projecting out of the grip part when the first and second projections are in engagement including a member positioned outside the grip part for moving the lamella relative to the grip part to disengage the first and second projections and permit a separation of the grip part and the tool parts.

6. An operating tool according to claim 5 comprising first and second resilient lamellas arranged so that the members thereof positioned outside the grip part can be moved towards each other to disengage the first and second projections.

7. An operating tool according to claim 5 wherein the sleeve is non-movably secured to the grip part.

8. An operating tool according to claim 7 wherein the hard, low-wear material comprises stainless steel.

9. An operating tool for use in an operating room comprising a grip part having a tubular opening and made of a hard, low-wear metal, a tool part including a portion insertable into the opening in the grip part for rotationally connecting the tool part and the grip part, and a snap connection for releasably securing the tool part to the grip part so that upon the release of the snap connection the tool part can be separated from the grip part, the snap connection comprising an axially extending resilient lamella having an inner end portion fixedly connected to the insertable portion of the tool part and a free outer end portion which projects out of the grip part when the tool part and the grip part are connected, the lamella being constructed of a resilient material and being arranged so that the free end portion of the lamella is resiliently biased away from the tool part, and first and second radially oriented projections pre-formed on the grip part and the free end portion of the lamella and arranged so that they engage each other and connect the tool part to the grip part when the insertable member is fully inserted in the opening, the free end portion of the lamella being manually engageable for moving the free end portion towards the tool part for disengaging the projections when the tool part is to be separated from the grip part.

10. An operating tool according to claim 9 wherein the lamella is defined by an elongated, tubular snap collar having first and second, opposite, axially running slits extending from a free end of the collar towards and ending short of the inner end to thereby form first and second, opposite lamellas the free ends of which can be resiliently moved towards each other for disengaging the projections.

* * * * *